United States Patent [19]

Lam et al.

[11] Patent Number: 4,567,157

[45] Date of Patent: Jan. 28, 1986

[54] PRODUCTION OF PHENOLS AND CATALYST THEREFOR

[75] Inventors: Chiu T. Lam, Sewell, N.J.; David M. Shannon, Midland, Mich.

[73] Assignee: The Dow Chemical Company, Midland, Mich.

[21] Appl. No.: 379,229

[22] Filed: May 17, 1982

[51] Int. Cl.$^4$ .................. B01J 27/14; C01B 15/16; C07C 37/00

[52] U.S. Cl. .................. 502/208; 423/306; 568/801

[58] Field of Search .................. 252/437; 423/306

[56] References Cited

U.S. PATENT DOCUMENTS

| | | | |
|---|---|---|---|
| 1,914,785 | 2/1928 | Oxley | 252/437 X |
| 2,298,931 | 10/1942 | Drenman | 252/435 X |
| 2,375,041 | 5/1945 | Schmerling et al. | 252/437 X |
| 2,391,508 | 12/1945 | Pines et al. | 252/437 X |
| 2,554,819 | 5/1951 | Eads | 252/437 X |
| 2,727,924 | 12/1955 | Peariman | 568/801 |
| 2,852,567 | 9/1958 | Barnard et al. | 568/801 |
| 3,301,906 | 1/1967 | Besozzi et al. | 252/437 X |
| 3,327,004 | 6/1967 | Noddings et al. | 252/437 X |
| 3,327,007 | 6/1967 | Noddings et al. | 252/437 X |
| 3,476,809 | 11/1969 | Steffgen | 252/437 X |
| 4,127,503 | 11/1978 | Yoshikawa et al. | 502/401 |
| 4,423,155 | 12/1983 | Bell et al. | 502/208 X |
| 4,436,835 | 3/1984 | Horie et al. | 502/208 |

FOREIGN PATENT DOCUMENTS 2321101  11/1974  Fed. Rep. of Germany ...... 252/437

*Primary Examiner*—John Doll
*Assistant Examiner*—William G. Wright
*Attorney, Agent, or Firm*—Douglas N. Deline; Norman L. Sims; Christopher John Rudy

[57] ABSTRACT

Multicomponent catalysts comprising copper, a metal selected from the group consisting of vanadium, chromium, manganese, iron, cobalt, nickel and zinc; and phosphate are employed for oxidizing an aromatic carboxylic acid to the corresponding phenol, e.g., benzoic acid to phenol.

5 Claims, No Drawings

PRODUCTION OF PHENOLS AND CATALYST THEREFOR

BACKGROUND OF THE INVENTION

This invention relates to the production of phenols, and more particularly to the oxidation of aromatic carboxylic acids to phenols and catalyst therefor.

In U.S. Pat. Nos. 2,737,026 and 2,852,567, there are described processes for producing phenols from aromatic carboxylic acids which employ a catalyst including copper oxide. The present invention is directed to an improved process and catalyst for oxidizing an aromatic carboxylic acid to a phenol.

SUMMARY OF THE INVENTION

In accordance with one aspect of the present invention, there is provided a multicomponent catalyst comprising copper, phosphorus present in the form of phosphate, and a metal selected from the group consisting of vanadium, manganese, iron, cobalt, nickel and zinc.

In accordance with another aspect of the present invention, there is provided an improved catalytic process for oxidizing an aromatic carboxylic acid having at least one carboxyl group substituted on the aromatic nucleus to the corresponding phenol in which the catalyst is comprised of the above-described multicomponent catalyst.

DETAILED DESCRIPTION OF THE INVENTION

The multicomponent catalyst of the invention comprises copper, phosphorus present in the form of phosphate, and at least one metal selected from the group consisting of vanadium, chromium, manganese, iron, cobalt, nickel or zinc. Preferred are catalysts comprising copper, zinc, and phosphate.

The copper and other metal components of the catalyst are present in an oxidation state suitable for catalyzing the reaction of an aromatic carboxylic acid to a phenol. Preferably, the copper and remaining metals are present in an oxidized form, e.g., either as phosphates or oxides.

Further preferred are such multicomponent catalysts that additionally comprise alkali metals or alkaline earth metals, also present in an oxidized state. A highly preferred multicomponent catalyst comprises five components: copper, zinc, lithium, magnesium and phosphate, all metals being present either as phosphate salts or as oxides.

Particularly preferred is the above multicomponent catalyst wherein the molar ratio Cu/Zn/P/Li/Mg is in the range of 1.0/0.1/0.1/0.1/0.1 to 1.0/4.0/4.0/4.0/6.0, and preferably within the range of 1.0/1.0/1.0/1.0/1.0 to 1.0/3.0/3.0/3.0/4.0.

The multicomponent catalyst of the invention can be employed in the absence or presence of a suitable support material. Thus, for example, the catalyst may be in the form of pellets, extrudates, etc., or supported on a support material. Suitable support materials include alumina, silica, magnesium oxide, zirconium oxide, silicon carbide and diatomaceous earth.

The catalyst may be prepared by a variety of procedures known in the art. Thus, for example, supported catalysts may be prepared by impregnation or spray drying. Alternatively, the catalyst components can be mixed and compacted in the form of pellets, extrudates, etc.

In an example illustrating the preparation of a supported catalyst by impregnation, water-soluble salts of the metals, such as the nitrates, are first dissolved in concentrated phosphoric acid or a mixture of concentrated phosphoric and nitric acids. The solutions are then employed to impregnate a suitable support, such as alpha-alumina. The impregnated support may then be dried and calcined to oxidize the metals. The technique is more fully described in the examples that follow.

After their preparation, the catalysts of the invention are particularly suitable for use as catalysts in the oxidation of an aromatic carboxylic acid to the corresponding phenol. Suitable aromatic carboxylic acids have at least one carboxyl group substituted on the aromatic nucleus, which is generally a benzene or naphthalene nucleus. Other ring substituent groups, such as alkyl, halo, etc., may also be present. The preferred starting materials are monocarboxylic acids such as benzoic and alkyl-substituted benzoic acids. A most preferred aromatic carboxylic acid is benzoic acid.

The oxidation is effected with molecular oxygen which can be provided as such or in admixture with other gases, e.g., as air. The oxygen is employed in at least stoichiometric proportions, however, lesser or greater amounts could be employed. In general, oxygen is employed in an amount to provide an oxygen to carboxyl group mole ratio of from about 1:1 to 10:1, and preferably from 1.5:1 to 5:1.

The reaction is generally effected in the vapor phase in the presence of steam as a diluent. The steam also functions to minimize the production of esters that result from the reaction of the carboxylic acid and the product phenol. The steam is generally provided in an amount corresponding to a water/carboxyl group mole ratio of 5:1 to 500:1 and preferably 10:1 to 100:1. Additional diluents such as nitrogen may also be present.

The oxidation is effected at temperatures of from about 200° C. to 400° C., and preferably from 260° C. to 350° C. The oxidation is generally effected at pressures above atmospheric pressure, with the pressure generally being from about 2 to 20 atmospheres.

The catalytic oxidation can be readily effected by the use of any one of a wide variety of vapor-solid contact systems, e.g., employing the catalyst as a fixed or fluidized bed or in a transfer line type of contact system. The above means for effecting the reaction and others should be apparent to those skilled in the art from the present teachings.

The particular advantage obtained according to the instant invention is to provide an active catalyst for the highly selective oxidation of aromatic carboxylic acids to phenolic compounds. Additionally, the catalysts of the invention are characterized by reduced loss or migration of copper from the catalyst. Advantageously, the catalysts produce less metallic contamination of the phenolic product as well as a reduction in disadvantageous effects caused by migrated copper, such as induced electrochemical corrosion of the reactor surface. Consequently, use of special and expensive materials for reactor construction in order to avoid corrosion may be avoided thereby greatly reducing the costs associated with the invented process.

The following examples are provided as further illustrative of the invention and are not to be construed as limiting.

EXAMPLE 1

Catalyst Preparation

A 180-ml aqueous solution was prepared from 41.54 g of $Cu(NO_3)_2 \cdot 2\frac{1}{2}H_2O$, 24.62 g of $LiNO_3$, 53.12 g of $Zn(NO_3)_2 \cdot 6H_2O$, 20.0 g of 85.2 percent $H_3PO_4$ and 20.0 g of concentrated $HNO_3$. 192.0 g of $Mg(NO_3)_2 \cdot 6H_2O$ was ground into fine powder and mixed thoroughly with 50.0 g Instarok ® cement and 120.0 g of powdered diatomaceous earth available commercially as Filter-Cel ®. The solution was added to the solid mixture and a uniform slurry was made. The slurry was extruded to $\frac{1}{4}''$ diameter cylindrical strands and dried at 150° C. in air for 24 hours. The extrudates were ground into 50–80 mesh. The particles were pressed into $\frac{1}{4}''$ tablets. The tablets were calcined in air at 400° C. for 18 hours. The finished catalysts had average bulk density 0.55 g/cc, crush strength 41.6 lb/in. and dimension $\frac{1}{4}'' \times \frac{1}{8}''$.

EXAMPLE 2

Catalyst Preparation

A 35-ml aqueous solution was prepared from 2.51 g of $Cu(NO_3)_2 \cdot 2\frac{1}{2}H_2O$, 1.50 g of $LiNO_3$, 3.21 g of $Zn(NO_3)_2 \cdot 6H_2O$, 10.85 g of $Mg(NO_3)_2 \cdot 6H_2O$, 1.24 g of 85.2 percent $H_3PO_4$ and 2.00 ml of concentrated $HNO_3$. Diatomaceous earth (Celite 21A, available commercially from Manville Corp.) was ground to 20–40 mesh as catalyst support. To 15.0 g of support, approximately 12 ml of solution was added to wet the surface of the particles. The catalyst was dried at 150° C. for 2 hours and cooled to room temperature. The wetting and drying procedures were repeated until the solution was used up. The catalyst was finally calcined at 400° C. in air for 40 hours. The finished catalyst weighed 20.32 g.

EXAMPLE 3

Phenol Production

Molten benzoic acid at 150° C. was pressurized by nitrogen through a capillary tube of 316 stainless steel to achieve the appropriate flow rate. Similarly, the calculated amount of water was pressurized to a vaporizer which was controlled at 250° C. Oxygen and nitrogen or air were mixed with benzoic acid and steam in a 310° C. preheating zone above the catalyst bed.

The catalyst of Example 1 (10.0 cc, 5.52 g) was charged into a 316 stainless steel fixed bed reactor (11/16" I.D. × 12" length). Molten benzoic acid at 150° C. (flow rate, 9.7 g/hr) steam at 250° C. (flow rate, 7.7 g/hr water at room temperature), air (flow rate, 37 cc/min at room temperature) and nitrogen (flow rate, 36.8 cc/min at room temperature) were introduced into the preheating zone. The catalyst bed was maintained at 310° C. and the reaction was carried out under ambient pressure, about 0–10 psig. The products and the unreacted benzoic acid were condensed and collected underneath the reactor.

The process was run 6 hours each day for 5 days and the catalysts regenerated after each run for 3 hours at temperatures under 450° C. in the presence of steam and limited amounts of oxygen.

Table I presents a typical 6-hour run result using the tablet catalyst.

TABLE I

| Time (hr) | Benzoic Acid Conversion % | Selectivity % Phenol | Benzene | Diphenyloxide |
|---|---|---|---|---|
| 1 | 52.05 | 39.61 | 3.40 | 2.74 |
| 2 | 27.29 | 84.87 | 8.75 | 6.38 |
| 3 | 26.11 | 84.32 | 8.91 | 6.82 |
| 4 | 24.74 | 82.91 | 10.35 | 6.74 |
| 5 | 25.06 | 83.22 | 10.14 | 6.64 |
| 6 | 23.22 | 83.07 | 10.11 | 6.82 |

EXAMPLE 4

The reaction conditions of Example 3 were substantially repeated employing the catalysts of Example 1 and Example 2. Table II shows the reaction conditions and the results of the process using the two catalysts. Each was run for five 6-hour cycles at 310° C. The benzoic acid conversion was averaged for each day's run. The amount of copper was analyzed at the beginning and end of the reaction. The data indicated there was no activity decline or Cu loss.

TABLE II

| Catalyst | Size | Bed vol | Benzoic Acid g/hr | $H_2O$ g/hr | Air cc/min | $N_2$ cc/min |
|---|---|---|---|---|---|---|
| Exam. 1 | $\frac{1}{4}''$ | 10.0 cc | 9.70 | 7.70 | 37.0 | 36.8 |
| Exam. 2 | 20–40 mesh | 8.3 cc | 9.70 | 5.83 | 36.2 | 30.2 |

| Time (day) | % Benzoic Acid Conversion | | | | | % Cu | |
|---|---|---|---|---|---|---|---|
| | 1 | 2 | 3 | 4 | 5 | fresh | used |
| Exam. 1 | 27.92 | 29.95 | 27.69 | 29.75 | 27.73 | 4.9 | 4.7 |
| Exam. 2 | 35.74 | 41.03 | 42.46 | 43.27 | 42.65 | 3.6 | 3.9 |

EXAMPLE 5

The catalyst of Example 2 was compared with a catalyst comprised only of copper, lithium and magnesium in the oxide forms. The comparative catalyst was prepared in the following manner. Diatomaceous earth (Celite 408 available commercially from Manville Corp.) was ground into 20–35 mesh as catalyst support. A 100-ml aqueous solution was prepared from 10.44 g of $Cu(NO_3)_2 \cdot 3H_2O$, 3.0 g of $LiNO_3$ and 43.38 g of $Mg(NO_3)_2 \cdot 6H_2O$ and 5 ml of concentrated $HNO_3$. To 60 g of the support, approximately 50 ml of solution was added to wet the surface of the particles. The catalysts were dried at 150° C. for 2 hours and cooled to room temperature. The rest of the solution was added to the surface of the catalyst and the catalyst was again dried at 150° C. for 2 hours. The catalysts were calcined at 400° C. in air for 16 hours. The finished catalyst weighed 70.22 g.

The catalyst of Example 2 was compared under substantially identical reaction conditions with the above prepared comparative catalyst. Table III shows the comparison between the two catalysts. A decline in benzoic acid conversion over time and a very substantial Cu loss were noticed for the comparative catalyst.

TABLE III

| | Reaction Conditions | | | | | |
|---|---|---|---|---|---|---|
| Size | (cc) Bed | °C. | Benzoic Acid | $H_2O$ | $O_2$ | $N_2$ |

TABLE III-continued

| Catalyst | (mesh) | Vol | Temp | g/hr | g/hr | cc/min | cc/min |
|---|---|---|---|---|---|---|---|
| Exam. 2 | 20-40 | 8.3 | 310 | 15.34 | 9.0 | 11.0 | 92.0 |
| Compar.* | 20-35 | 8.3 | 310 | 15.34 | 9.0 | 11.0 | 92.0 |

Results
% Benzoic Acid Conversion

| Time (day) | 1 | 2 | 3 | 5 | 7 | 9 | 18 |
|---|---|---|---|---|---|---|---|
| Exam. 2 | 32.20 | 34.83 | 33.71 | — | — | 33.31 | — |
| Compar.* | 30.04 | — | — | 31.49 | 23.41 | 20.93 | 9.61 |

*Comparative

After completion of the reaction, the comparative catalyst was analyzed for loss of copper during the reaction. If was found that the comparative catalyst contained 3.5 percent weight copper initially, but only 0.6 percent by weight after completion of the reaction. Under substantially the same reaction conditions, no loss of copper was observed for the catalyst according to Example 2.

What is claimed is:

1. A multicomponent catalyst consisting essentially of copper, phosphorus present in the form of phosphate, and a metal selected from the group consisting of vanadium, chromium, manganese, iron, cobalt, nickel and zinc.

2. A catalyst of claim 1 additionally comprising a support material.

3. A multi-component catalyst consisting essentially of copper, phosphorus present in the form of a phosphate, zinc, and an alkali metal or both an alkali metal and an alkaline earth metal.

4. A catalyst of claim 3 wherein the catalyst consists essentially of copper, zinc, lithium, magnesium and phosphate.

5. A catalyst of claim 4 wherein copper, zinc, phosphorus, lithium and magnesium are present in a ratio from 1/0.1/0.1/0.1/0.1 to about 1/4/4/4/6.

* * * * *

UNITED STATES PATENT AND TRADEMARK OFFICE
CERTIFICATE OF CORRECTION

PATENT NO. : 4,567,157

DATED : January 28, 1986

INVENTOR(S) : Chiu T. Lam, Sewell, N.J.; David M. Shannon, Midland, Mich.

It is certified that error appears in the above-identified patent and that said Letters Patent is hereby corrected as shown below:

Column 5, line 17, the word "If" should be --It--.

Column 6, lines 6-7, delete "a metal selected from the group consisting of vanadium, chromium, manganese, iron, cobalt, nickel and."

Signed and Sealed this

Twenty-ninth Day of November, 1988

Attest:

DONALD J. QUIGG

Attesting Officer

Commissioner of Patents and Trademarks